(12) United States Patent
Lin et al.

(10) Patent No.: US 11,484,356 B2
(45) Date of Patent: Nov. 1, 2022

(54) PLASMA OPERATION ELECTRODE FOR OTOLARYNGOLOGY DEPARTMENT

(71) Applicant: SIMAI CO., LTD., Guangdong (CN)

(72) Inventors: Min Lin, Guangdong (CN); Jiancong Wu, Guangdong (CN)

(73) Assignee: SIMAI CO., LTD., Zhuhai (CN)

( * ) Notice: Subject to any disclaimer, the term of this patent is extended or adjusted under 35 U.S.C. 154(b) by 305 days.

(21) Appl. No.: 16/703,920

(22) Filed: Dec. 5, 2019

(65) Prior Publication Data

US 2021/0059741 A1    Mar. 4, 2021

(30) Foreign Application Priority Data

Aug. 30, 2019   (CN) .......................... 201910813591.7

(51) Int. Cl.
*A61B 18/04* (2006.01)
*A61B 18/14* (2006.01)
*A61B 18/00* (2006.01)

(52) U.S. Cl.
CPC ........ *A61B 18/042* (2013.01); *A61B 18/1485* (2013.01); *A61B 2018/0013* (2013.01); *A61B 2018/00077* (2013.01); *A61B 2018/00327* (2013.01); *A61B 2018/00601* (2013.01)

(58) Field of Classification Search
CPC .............. A61B 18/042; A61B 18/1485; A61B 2018/00077; A61B 2018/0013; A61B 2018/00327; A61B 2018/00601
See application file for complete search history.

(56) References Cited

U.S. PATENT DOCUMENTS

| 4,682,596 A | * | 7/1987 | Bales ................. A61B 18/1492 606/39 |
| 5,556,397 A | * | 9/1996 | Long ................. A61B 18/1402 606/50 |
| 5,683,366 A | * | 11/1997 | Eggers ................. A61B 18/12 604/114 |

(Continued)

FOREIGN PATENT DOCUMENTS

| CN | 201907566 U | 7/2011 |
| CN | 203122593 U | 8/2013 |

(Continued)

*Primary Examiner* — Linda C Dvorak
*Assistant Examiner* — Annabeth E Rodriguez (57) ABSTRACT

The present invention discloses a plasma operation electrode for an otolaryngology department. The plasma operation electrode for the otolaryngology department includes a tubular loop electrode, a water absorption tube and an effluent flow guiding component. The water absorption tube is sheathed in the tubular loop electrode, a water inlet channel is formed between the water absorption tube and the tubular loop electrode. An end part, away from the handle, of the tubular loop electrode is provided with at least one water outlet hole. The effluent flow guiding component is correspondingly installed at the water outlet hole, and sealed and connected on an outer wall of the tubular loop electrode. A water injecting channel is formed between the effluent flow guiding component and the tubular loop electrode. The plasma operation electrode for the otolaryngology department has a good flow guiding effect to normal saline, and high in reliability and safety.

10 Claims, 9 Drawing Sheets

(56) References Cited

U.S. PATENT DOCUMENTS

| | | | |
|---|---|---|---|
| 7,442,191 B2 | 10/2008 | Hovda et al. | |
| 7,566,333 B2 * | 7/2009 | Van Wyk | A61B 18/1485 606/41 |
| 2004/0199157 A1 * | 10/2004 | Palanker | A61B 18/042 606/41 |
| 2006/0253117 A1 * | 11/2006 | Hovda | A61B 18/1492 606/50 |
| 2007/0181043 A1 * | 8/2007 | Heim | B05D 1/36 106/815 |
| 2008/0065062 A1 * | 3/2008 | Leung | A61B 18/148 606/41 |
| 2016/0143683 A1 * | 5/2016 | Aluru | A61B 18/042 606/41 |

FOREIGN PATENT DOCUMENTS

| | | | | |
|---|---|---|---|---|
| CN | 203677241 U | | 7/2014 | |
| CN | 107137140 A | * | 9/2017 | ............. A61B 18/02 |
| CN | 107137140 A | | 9/2017 | |
| WO | 2015156157 A1 | | 10/2015 | |

* cited by examiner

PLASMA OPERATION ELECTRODE FOR OTOLARYNGOLOGY DEPARTMENT

CROSS REFERENCE TO RELATED APPLICATIONS

The present application claims the benefit of Chinese Patent Application No. 201910813591.7 filed on Aug. 30, 2019, the contents of which are incorporated herein by reference in their entirety.

TECHNICAL FIELD

The present invention relates to the technical field of medical equipment, and particularly relates to a plasma operation electrode for an otolaryngology department.

BACKGROUND

A low-temperature plasma ablation technology, because it has the advantages of safety, minimally invasive, simple operation, small pain of a patient and the like, and is capable of achieving the functions of cutting, ablation and hemostasis and the like to a tissue in a low-temperature (40-70 DEG C.) condition, is more and more applied in clinical practice, especially in an otolaryngology department, it has a very extensive application in the cutting, the ablation and the hemostasis and the like of tonsil and adenoid resection operations. A fundamental principle of the technology is that an electric field in certain frequency is used, electrolyte between a plasma operation electrode and a target tissue is converted into a low-temperature plasma state, a highly aggregated plasma thin layer is formed at a front end of the operation electrode, the strong electric field is capable of enabling free charged particles in the plasma thin layer to acquire enough energy, and transmitting the energy to the target tissue, a molecular bond for forming a cell component in the target tissue is disaggregated, cells in the target tissue are disintegrated by using a molecule as a unit, and decomposed into a carbohydrate and an oxide, and coagulation necrosis of the tissue is caused, thereby ablation and cutting effects are achieved. A low-temperature plasma ablation operation belongs to a minimally invasive surgery, safety of a local mucous membrane tissue structure may be maintained, and post-operation edema and pain may be effectively relieved. Ablation time is very short, a post-operation symptom may be relieved in about 15-20 minutes, and may not be relapsed generally after the operation. The low-temperature plasma ablation operation is suitable for shaping, cutting and blood coagulating of various tissues of a human body, an operation process is safe and painless, and amygdalitis, sleep apnea syndrome, pharyngitis and the like may be effectively treated.

Figure 1:
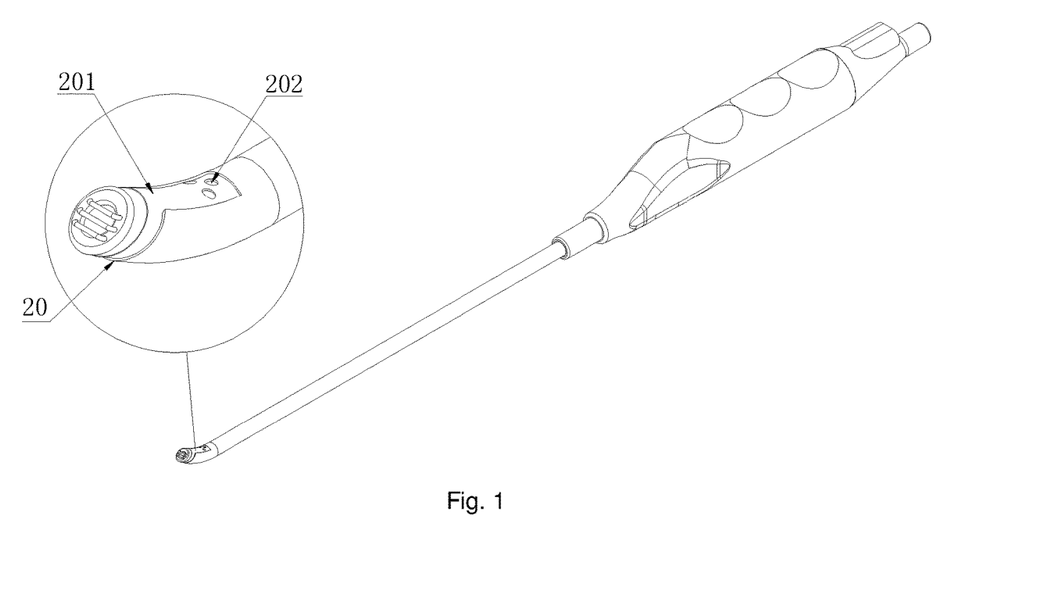
FIG. 1 is a structure schematic diagram of a plasma operation electrode in an existing technology.
Figure 2:
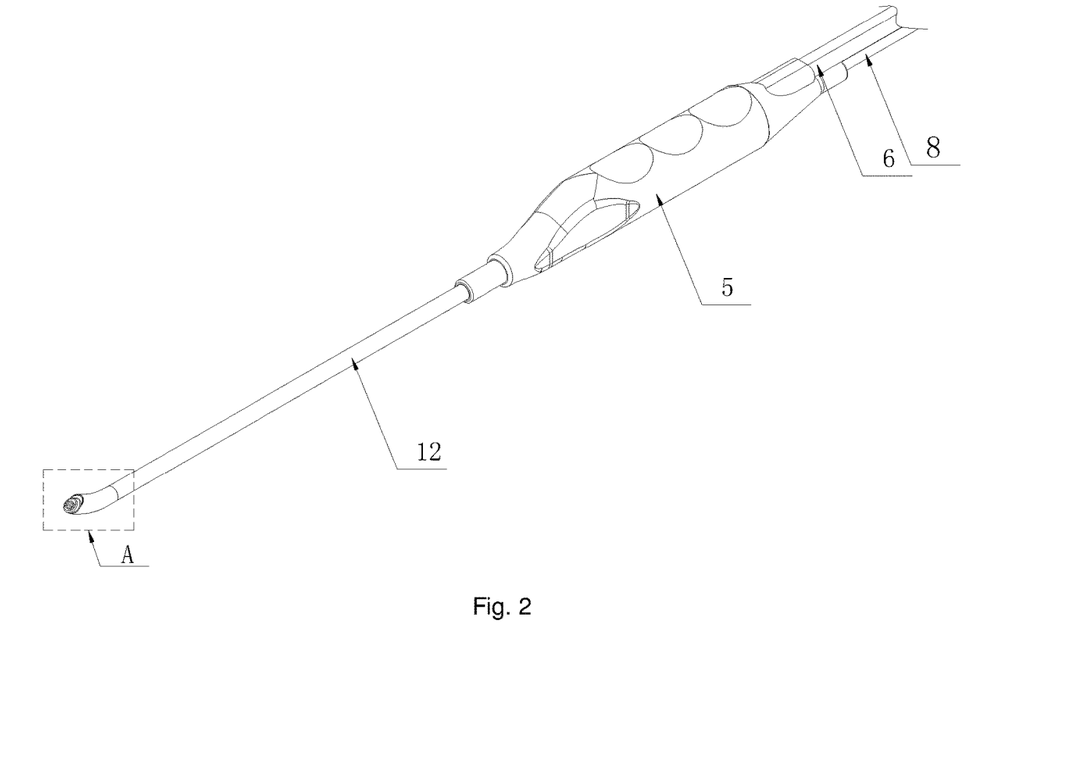
FIG. 2 is a structure schematic diagram of a plasma operation electrode for an otolaryngology department of an embodiment of the present invention.

The plasma operation electrode is an operation instrument designed in order to achieve the low-temperature plasma operation, the plasma operation electrode is capable of generating a high-frequency and high-pressure repetitive pulse through using a modern electronic technology, and forming luminous plasma for discharging among the electrode in normal saline, in an incentive function of a strong electric field, achieving a purpose of tissue cutting, ablation and blood coagulating. In the plasma surgical operation, the normal saline is further used as a medium formed by plasma, besides used for maintaining electrolyte balance of a tissue, and cleaning up a wound, and a state of the normal saline plays a very important role in the plasma surgical operation. An effluent structure of the normal saline is rational or not is a key problem of affecting a normal saline conveying effect, a washing effect and electrical conductivity. As shown in FIG. 1, at present, an existing plasma operation electrode applied to tonsil and adenoid is generally that a lower side 201 of an external electrode 20 exposed out of an insulating layer is provided with a flow guiding hole 202, and the normal saline is discharged through the flow guiding hole 202, while such a structure is used, the following problems exists: because a metal end of the external electrode 20 is exposed out of the insulating layer, not only a potential safety hazard of easy current leakage exists, but also an exposed head of the external electrode 20 is easy to scald tissues of other parts, irritation is large, and a risk is high, it is easy to cause large mental stress of a doctor and a patent, thereby poor reliability, safety and stability of the operation are caused; otherwise, the flow guiding hole 202 is installed on the external electrode 20, on the one hand, water supply capacity is insufficient, and water supply is non-uniform, on the other hand, the normal saline is flowed to a water inlet place of a head end of the working electrode only dependent on water flow pressure and gravity action, so feed liquid of the head end of the electrode is unstable and uncontrollable, especially while the head end of the electrode is not downward vertically, particularly while the head end of the electrode is upward, the normal saline may not be accurately flowed to the water inlet place of the head end of the working electrode, a situation that the electrode is unstable in work even stopped is caused, insufficient feed liquid of the normal saline at the head end of the electrode may also cause an excess temperature so as to injure the tissue, and the insufficient feed liquid of the working saline at the head end of the electrode may generate a lot of smoke so as to affect definition of an operation view; at the same time, after the insulating layer adjacent to a working electrode end is used for multiple times, deformation is easily generated so as to cause a problem of poor water supply. Otherwise, in the operation, if the treatment operation needs to be simultaneously performed on the tonsil and the adenoid, because the electrode for the tonsil operation in an existing technology is difficult to achieve the operative treatment of the adenoid, another special electrode needs to be replaced, it is very inconvenient.

Therefore, it is very necessary to research and develop a plasma operation electrode for an otolaryngology department which is reliable in water supply, universal, no current-leakage, and high safety.

SUMMARY

In order to overcome deficiency of an existing technology, the present invention aims to provide a plasma operation electrode for an otolaryngology department, the operation electrode has a good flow guiding effect to normal saline, and is uniform and adequate in water supply, capable of effectively enhancing electrical conductivity, effectively guaranteeing no current leakage in a position of contacting a tissue, and high reliability and safety.

In order to solve the above problems, a technical scheme used by the present invention is as follows:

A plasma operation electrode for an otolaryngology department, herein the plasma operation electrode for the otolaryngology department includes an insulating head, a working electrode, a tubular loop electrode, a water absorption tube, a handle, a water inlet hose, a water outlet hose and a lead; a reflowing hole is internally provided in the insulating head, one end of the insulating head is provided with the working electrode, and the other end of the insulating head is fixedly connected with an end part of the handle through the tubular loop electrode; the water absorption tube is sheathed in the tubular loop electrode, a water inlet channel is formed between the water absorption tube and the tubular loop electrode, and an end part of the water absorption tube is connected with the insulating head and communicated with the reflowing hole; the water inlet hose is installed in the handle and communicated with the tubular loop electrode, the water outlet hose is installed in the handle and communicated with the water absorption tube, and the lead passes through the handle and is connected with the tubular loop electrode, herein the plasma operation electrode for the otolaryngology department further includes an effluent flow guiding component. An end part, away from the handle, of the tubular loop electrode is provided with at least one water outlet hole. The effluent flow guiding component is correspondingly installed at the water outlet hole, and sealed and connected on an outer wall of the tubular loop electrode. A water injecting channel is formed between the effluent flow guiding component and the tubular loop electrode.

It may be seen from the above scheme, the operation electrode of the present invention is capable of, through installing the effluent flow guiding component in the position, corresponding to the water outlet hole, of the tubular loop electrode, enabling an effluent water flow direction to be changed, thereby guiding the normal saline to the working electrode of the insulating head, so the water supply of the normal saline is uniform, the water supply capacity is sufficient, the feed liquid is controllable and stable, and conductive continuity may be guaranteed so that the electrical conductivity is effectively enhanced, the effectiveness, safety and stability of the plasma operation electrode for the otolaryngology department are improved in a certain degree. Otherwise, the plasma operation electrode of the present invention may be suitable for a resection operation of the tonsil and the adenoid, universality is strong, and consumable cost is saved.

As an optimized embodiment of the present invention, one end of the effluent flow guiding component is connected to the outer wall of the tubular loop electrode, the other end is extended to the end part, provided with the working electrode, of the insulating head, it may be effectively guaranteed that the normal saline is flowed to the working electrode along the outer wall of the insulating head through inertia, and the electrical conductivity is further increased.

As an optimized embodiment of the present invention, outer surfaces of the effluent flow guiding component and the tubular loop electrode are coated with an insulating layer except for the connecting position of the two parts, so that the tubular loop electrode is completely sealed, a problem that a traditional tubular loop electrode generates current stimulation or accident scald to a peripheral tissue because a part is exposed is well solved, and a problem in an existing technology that deformation is generated so as to cause poor water supply after the insulating layer is used for multiple times is well avoided.

As an optimized embodiment of the present invention, the effluent flow guiding component is an arc-shaped effluent flow guiding sheet; the water outlet hole is installed in a lower side of the tubular loop electrode, and the effluent flow guiding component is correspondingly sealed and installed at the lower side of the tubular loop electrode; and the water injecting channel is formed between the effluent flow guiding component and the tubular loop electrode.

As another optimized embodiment of the present invention, the effluent flow guiding component is the arc-shaped effluent flow guiding sheet; the end part, away from the handle, of the tubular loop electrode is provided with two water outlet holes, the water outlet holes are installed at upper side and lower side of the tubular loop electrode, the effluent flow guiding component is correspondingly sealed and installed at the upper side and lower side of the tubular loop electrode, and corresponds to positions of the two water outlet holes; and the water injecting channel is respectively formed between the effluent flow guiding component and the upper side of the tubular loop electrode and between the effluent flow guiding component and the lower side of the tubular loop electrode.

As a third optimized embodiment of the present invention, the end part, away from the handle, of the tubular loop electrode is symmetrically provided with at least two water outlet holes; the effluent flow guiding component is a tubular structure, the effluent flow guiding component is sealed and sheathed in a position, corresponding to the water outlet holes, of the tubular loop electrode, and a cross section of the water injecting channel which is formed between the effluent flow guiding component and the tubular loop electrode is annular.

As an optimized embodiment of the present invention, a width of the water injecting channel is 2.5-4.2 mm, and a height is 0.2-1 mm.

As an optimized embodiment of the present invention, a front end part, away from the handle, of the tubular loop electrode is a curved structure, and an included angle Alpha between a central axis of the front end part of the tubular loop electrode and an axis of the water outlet hole is 45-60 degrees.

As an optimized embodiment of the present invention, the effluent flow guiding component and the tubular loop electrode are made of stainless steel with good electrical conductivity, and the effluent flow guiding component is welded and fixed with the tubular loop electrode.

As an optimized embodiment of the present invention, the working electrode is provided with an oleophobic layer.

Compared with the existing technology, the beneficial effect of the present invention is as follows.

The plasma operation electrode for the otolaryngology department of the present invention is capable of, through installing the effluent flow guiding component in the position, corresponding to the water outlet hole, of the tubular loop electrode, changing a supply water flow direction and forming an arc-shaped water flow, thereby guiding the normal saline to the working electrode along the outer wall of the insulating head, so the water supply of the normal saline is uniform and reliable, the feed liquid is controllable and stable, and guaranteed, the conductivity of the electrode is enhanced, conductive working continuity of the electrode is effectively guaranteed, the effectiveness, safety and stability of the operation electrode are improved in a certain degree, and operation time is saved. Otherwise, the present invention is capable of, through cooperation of the effluent flow guiding component and the insulating layer, enabling the tubular loop electrode to be completely sealed, there is no current leakage, so a problem that a traditional tubular loop electrode generates current stimulation or accident scald to a peripheral tissue because a part is exposed is well solved, and a problem in an existing technology that deformation is generated so as to cause poor water supply after the insulating layer is used for multiple times is well avoided. Otherwise, the plasma operation electrode of the present invention may be suitable for a resection operation of the tonsil and the adenoid, universality is strong, and consumable cost is saved.

In conclusion, the operation electrode of the present invention has the good flow guiding effect to the normal saline, sufficient feed liquid, and effective work may be ensured while the electrode is positioned in any directions, the treatment to all-dimensional target tissues may be achieved, and the problem that the traditional tubular loop electrode generates the current stimulation or accident scald to the peripheral tissue because a part is exposed is avoided, the reliability and safety are high, use is convenient, the operation electrode may be simultaneously suitable for the resection operation of the tonsil and the adenoid, and the universality is strong.

Drawing mark description: 1, insulating head; 101, lower side of the insulating head; 102, upper side of the insulating head; 103, reflowing hole; 2, working electrode; 3, tubular loop electrode; 301, through hole; 4, water absorption tube; 5, handle; 6, water inlet hose; 7, water outlet hose; 8, lead; 9, effluent flow guiding component; 10, water outlet hole; 11, water injecting channel; 12, insulating layer; 13, connector; 20, external electrode; 201, lower side of the external electrode; and 202, flow guiding hole.

DETAILED DESCRIPTION OF THE EMBODIMENTS

The present invention is further described in detail below in combination with the drawings and specific implementation modes.

As shown in FIG. 2 to FIG. 5, the plasma operation electrode for the otolaryngology department of the present invention includes an insulating head 1, a working electrode 2, a tubular loop electrode 3, a water absorption tube 4, a handle 5, a water inlet hose 6, a water outlet hose 7 and a lead 8.

A reflowing hole 103 is internally provided in the insulating head 1, and penetrates through the insulating head 1 along a radial direction of the insulating head 1, and is used for reflowing normal saline; a front end of the insulating head 1 is provided with the working electrode 2, a rear end of the insulating head 1 is fixedly connected with an end part of the handle 5 through the tubular loop electrode 3, the working electrode 2 and the tubular loop electrode 3 are isolated by the insulating head 1, so an insulating effect is achieved. In the present embodiment, the insulating head 1 is made of ceramics, in other embodiments, the insulating head 1 is also made of other insulating materials, for example, high-temperature resistance plastics of PTFE, PEEK, PI and the like or insulating materials of quartz stone and the like.

The working electrode 2 includes three electrode wires, and end parts of the three electrode wires are uniformly and parallelly embedded in a central position of a front end part of the insulating head 1 after bended.

A front end of the tubular loop electrode 3 is fixedly connected with the insulating head 1, and a rear end part is inserted in the handle 5 and sealed and fixed through a connector 13, the lead 8 is installed in the handle 5, one end of the lead 8 is connected with an outer wall of the tubular loop electrode 3, and the other end is connected with an external power source, power is supplied to the tubular loop electrode 3 through the lead 8. A part, inserted in the handle 5, of the tubular loop electrode 3 is provided with a through hole 301, and the through hole 301 is communicated with the water inlet hose 6 installed in the handle 5, so a water inlet pipeline is formed.

The water absorption tube 4 is sheathed in the tubular loop electrode 3, a water inlet channel 14 is formed between the water absorption tube 4 and the tubular loop electrode 3, and the water inlet channel is communicated with the water inlet pipeline, so the saline is flowed into the water inlet channel from the water inlet pipeline through the through hole 301. One end part of the water absorption tube 4 is connected with the insulating head 1 and communicated with the reflowing hole 103 of the insulating head 1, and the other end part is inserted in the connector 13 for fixing and communicated with the water outlet hose 7 in the handle 5, the saline enters the water absorption tube 4 through the reflowing hole 103 after liquid is supplied, and is flowed into the water outlet hose 7.

The plasma operation electrode for the otolaryngology department of the present invention further includes an effluent flow guiding component 9. A front end part, away from the handle 5, of the tubular loop electrode 3 is provided with at least one water outlet hole 10, the effluent flow guiding component 9 is correspondingly installed at the water outlet hole 10, and sealed and connected to an outer wall of the tubular loop electrode 3, a water injecting channel 11 which has a crescent shaped cross section is formed between the effluent flow guiding component 9 and the tubular loop electrode 3, the saline enters the water inlet pipeline from the water inlet hose 6, enters the water inlet channel through the through hole 301, then enters the water injecting channel 11 through the water outlet hole 10, and is discharged from a front end part of the effluent flow guiding component 9.

The present invention is capable of, through installing the effluent flow guiding component 9, changing the water flow direction, and enabling the normal saline which is flowed along a radial direction of the insulating head 1 to be flowed in arc shape around an inner wall of the effluent flow guiding component 9 after flowed through the water outlet hole 10, thereby guiding the normal saline to the working electrode 2 of the insulating head 1, so the normal saline is uniformly supplied around a circumferential direction of the insulating head 1, water supply capacity is sufficient, feed liquid is controllable and stable, and conductive continuity may be guaranteed so that electrical conductivity is effectively enhanced, at the same time, a temperature of the working electrode 2 is guaranteed to be moderate in operation, scald or blackening of a contacted human tissue caused by an excess temperature is avoided, and the reliability, safety and stability of the plasma operation electrode for the otolaryngology department are improved in a certain degree.

Further, a front end part of the effluent flow guiding component 9 is extended to a front end part of the insulating head 1, so the front end part of the effluent flow guiding component 9 is aligned to the front end part of the insulating head 1, or the front end part of the insulating head 1 is protruded from the front end part of the effluent flow guiding component 9, thereby it may be guaranteed that the normal saline is flowed to the working electrode 2 along an outer wall of the insulating head 1 through inertia, and the electrical conductivity is further increased. More further, outer surfaces of the effluent flow guiding component 9 and the tubular loop electrode 3 are coated by an insulating layer 12, except for the connecting part of the two parts, so that the tubular loop electrode 3 is completely sealed, a problem that other parts of tissues are accidently scalded because the tubular loop electrode 3 is exposed is well avoided, and a problem in an existing technology that deformation is generated so as to cause poor water supply after the insulating layer 12 is used for multiple times is well avoided.

Figure 3:
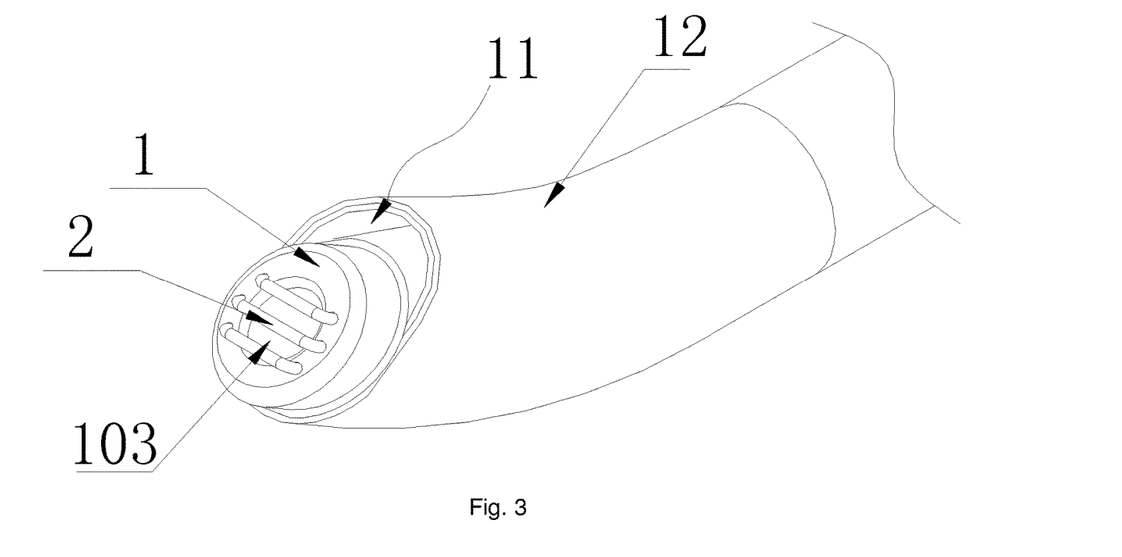
FIG. 3 is an enlarged drawing of a part A in FIG. 1 of the present invention.
Figure 4:
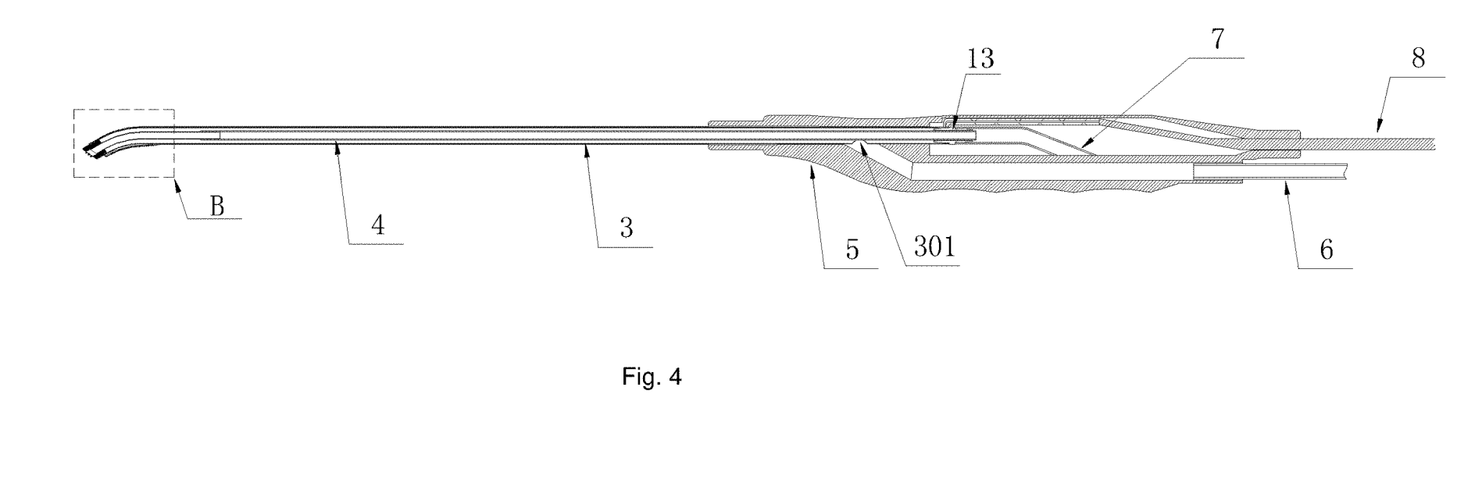
FIG. 4 is a section view of the plasma operation electrode for the otolaryngology department in FIG. 1.
Figure 5:
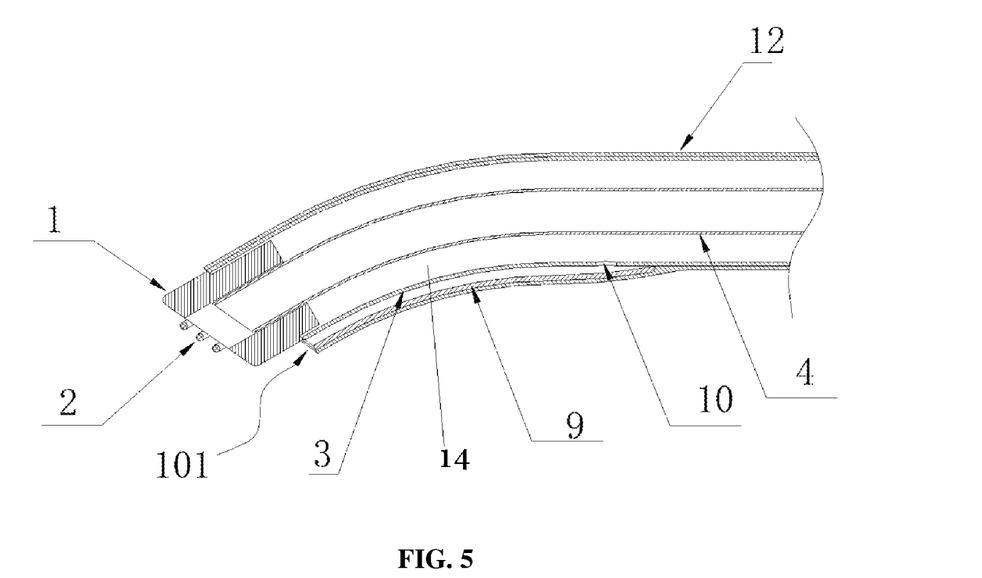
FIG. 5 is an enlarged drawing of a part B in FIG. 3 of the present invention.
Figure 6:
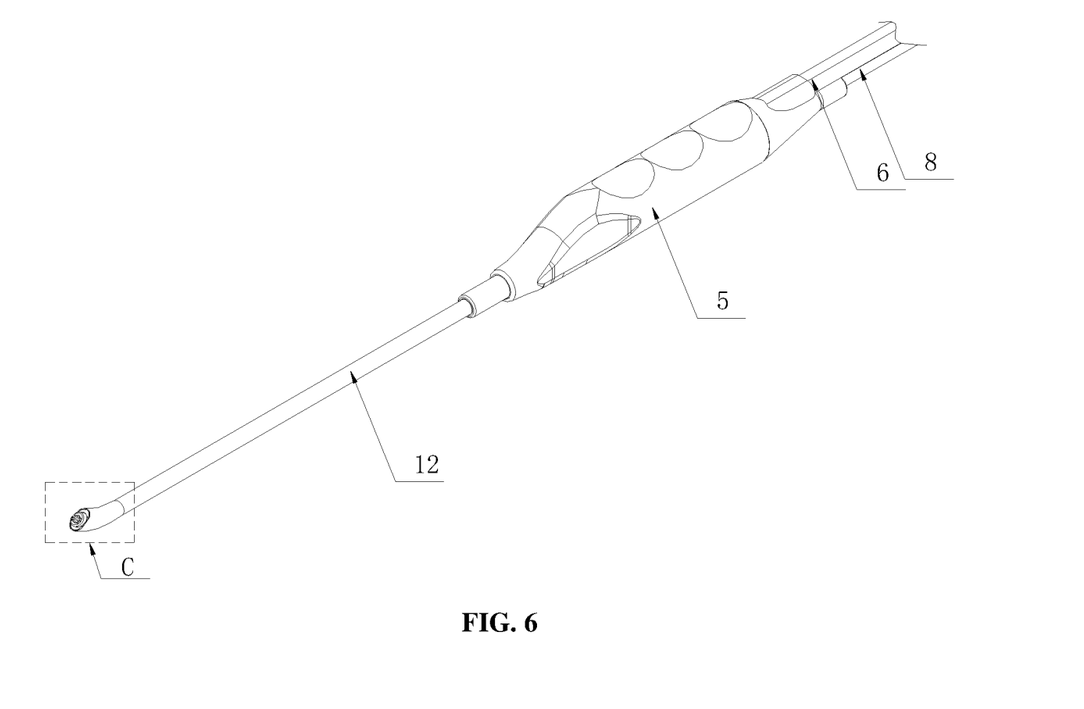
FIG. 6 is a structure schematic diagram of a plasma operation electrode for an otolaryngology department of another embodiment of the present invention.
Figure 7:
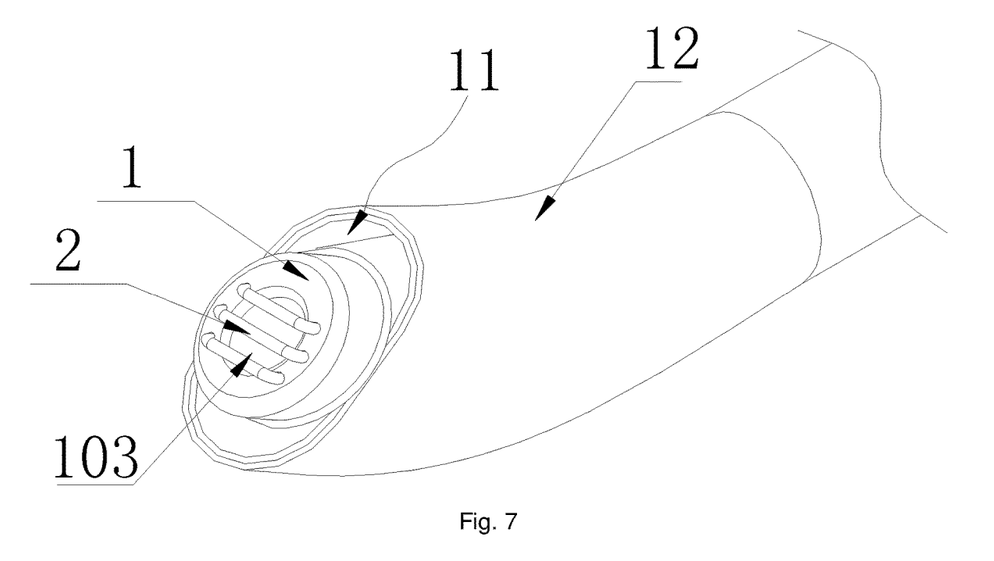
FIG. 7 is an enlarged drawing of a part C in FIG. 6 of the present invention.
Figure 8:
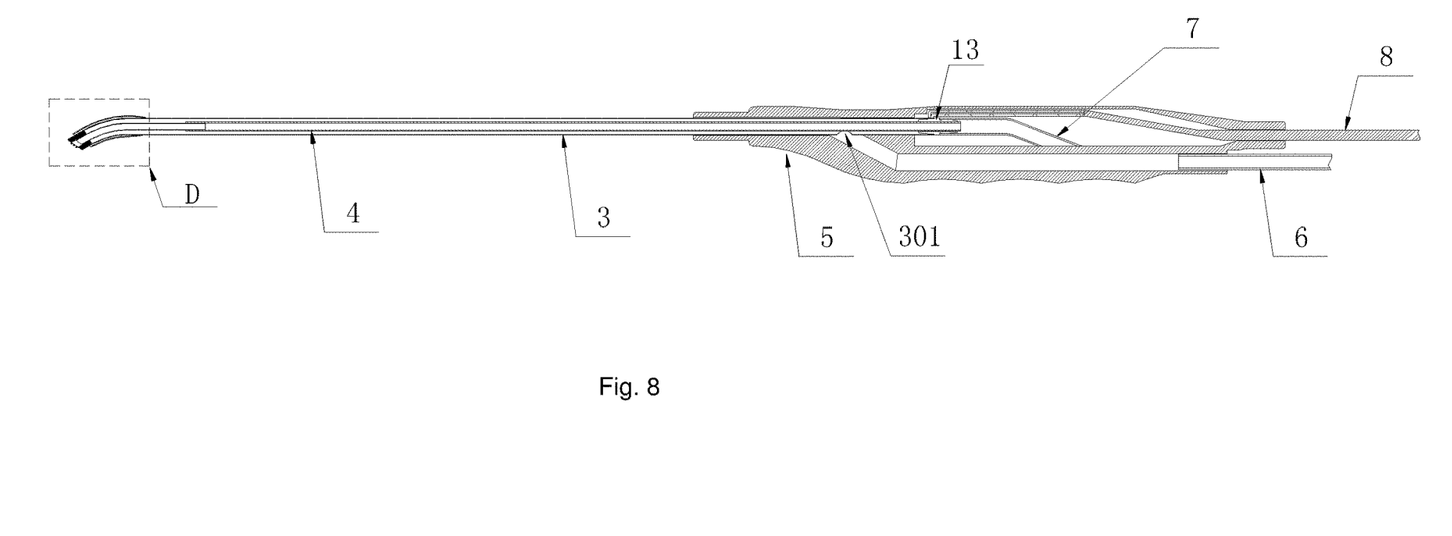
FIG. 8 is a section view of the plasma operation electrode for the otolaryngology department in FIG. 6 of the present invention.
Figure 9:
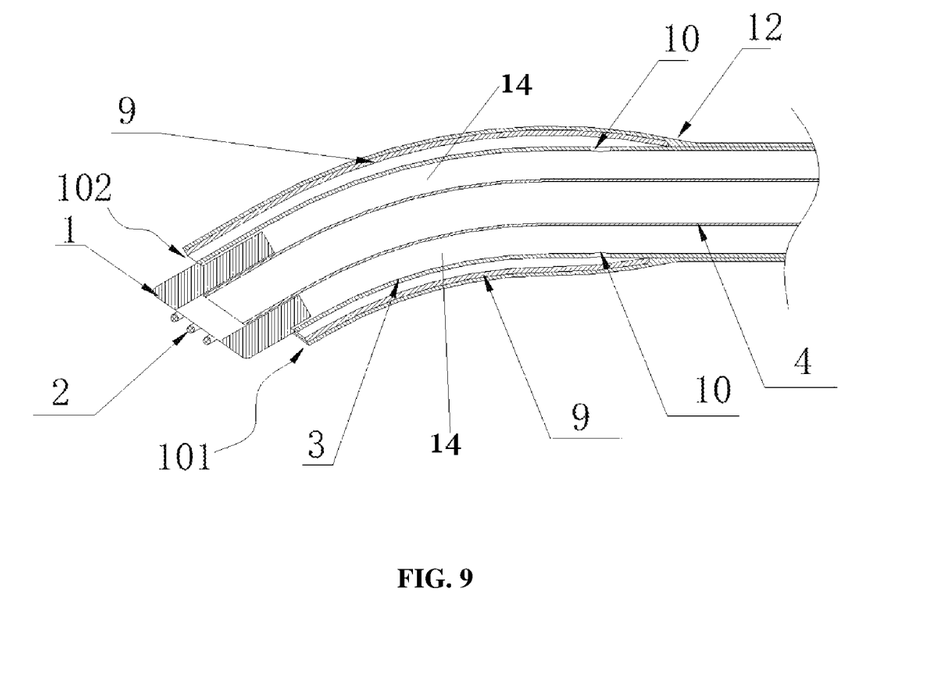
FIG. 9 is an enlarged drawing of a part D in FIG. 8 of the present invention.

As shown in FIG. 3, in an optimized embodiment of the present invention, the effluent flow guiding component 9 is an arc-shaped effluent flow guiding sheet; the water outlet hole 10 is installed in a lower side of the tubular loop electrode 3, and the effluent flow guiding component 9 is correspondingly sealed and installed at the lower side of the tubular loop electrode 3; and a water injecting channel 11 which has a crescent shaped cross section is formed between the effluent flow guiding component 9 and the tubular loop electrode 3, the water injecting channel 11 is positioned at a lower side 101 of the insulating head, it means, the water injecting channel 11 is positioned at an inner arc side of a curved part of the front end part of the tubular loop electrode 3, such a structure is capable of enabling the normal saline to be guided to the working electrode 2 at the front end of the insulating head 1 along the inner arc side of the tubular loop electrode 3 through using gravity, adequately supplying water, and advantageously keeping continuity of water supply, thereby enhancing the electrical conductivity, and improving the effectiveness, safety and stability of the operation electrode, in addition, the operation electrode may be simultaneously suitable for resection operations of tonsil and adenoid, the operation electrode does not need to be replaced in an operation process, the continuity of the surgical operation of a doctor is effectively guaranteed, consumable cost is saved, and efficiency of the operation is improved.

As shown in FIG. 6 to FIG. 9, in another embodiment of the present invention, the effluent flow guiding component 9 is the arc-shaped effluent flow guiding sheet; a position, adjacent to the front end part, of the tubular loop electrode 3 is provided with two water outlet holes 10, the two water outlet holes 10 are respectively installed at upper side and lower side of the tubular loop electrode 3, the effluent flow guiding component 9 is correspondingly sealed and installed at the upper side and lower side of the tubular loop electrode 3, and installed corresponding to positions of the two water outlet holes 10; the water injecting channel 11 which has a crescent shaped cross section is respectively formed between the effluent flow guiding component 9 and the upper side of the tubular loop electrode 3 and between the effluent flow guiding component 9 and lower side of the tubular loop electrode 3, the water injecting channel 11 is positioned at the lower side 101 and upper side 102 of the insulating head, on the one hand, the water supply capacity is more sufficient, and the water supply is more uniform, on the other hand, the conductive continuity is more reliable. Certainly, while the position, adjacent to the end part, of the tubular loop electrode 3 is provided with two water outlet holes 10, the water outlet holes 10 may also be installed at left side and right side of the tubular loop electrode 3, the effluent flow guiding component 9 is correspondingly sealed and installed at the left side and right side of the effluent flow guiding component 9, the above effect may be achieved too.

Figure 10:
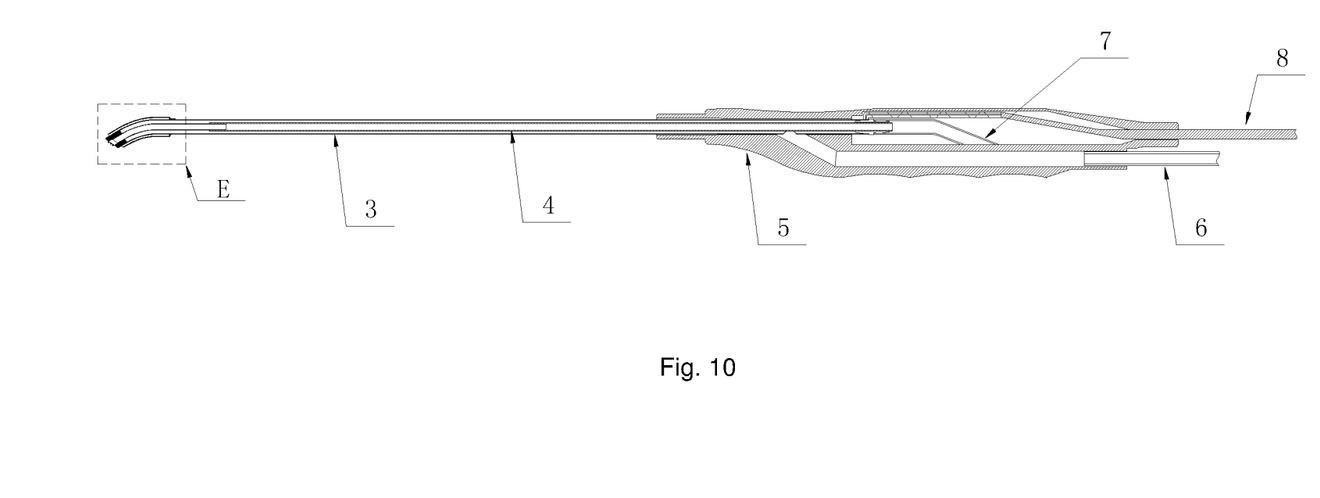
FIG. 10 is a structure schematic diagram of a plasma operation electrode for an otolaryngology department of a third embodiment of the present invention.
Figure 11:
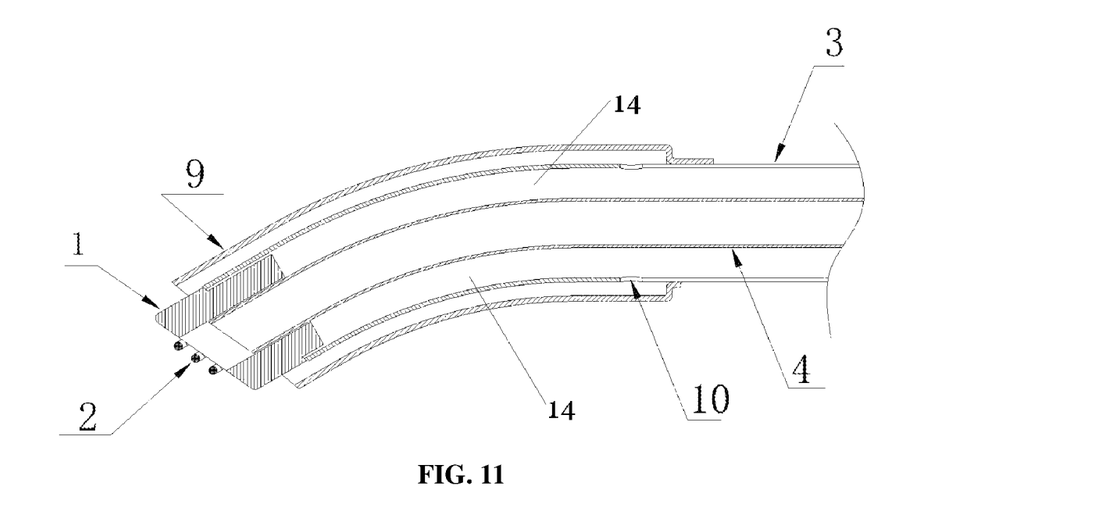
FIG. 11 is an enlarged drawing of a part E in FIG. 10 of the present invention.

Positions of the effluent flow guiding component 9 and the water outlet holes 10 on the tubular loop electrode 3 may be set according to the actual needs, and are not limited to the above embodiments, only if the normal saline may be guided to the front end part of the insulating head 1 and the tubular loop electrode 3 may be completely coated, it is accepted. For example, the effluent flow guiding component 9 and the water outlet holes 10 may be set according the following embodiments: as shown in FIG. 10 to FIG. 11, the position, adjacent to the front end part, of the tubular loop electrode 3 is symmetrically provided with at least two water outlet holes 10; the effluent flow guiding component 9 is a tubular structure, the effluent flow guiding component 9 is correspondingly sealed and sheathed in a position, corresponding to the water outlet holes 10, of the tubular loop electrode 3, and a cross section of the water injecting channel 11 which is formed between the effluent flow guiding component 9 and the tubular loop electrode 3 is annular, such a structure is capable of enabling the normal saline to be uniformly supplied along the annular water injecting channel 11 through the water outlet holes 10; and the insulating layer 12 in the embodiment is not shown in the drawings.

An under size of the water injecting channel 11 may cause insufficient water supply so that the electrode may not be normally used, and an excessive size of the water injecting channel 11 may block a view in operation, thereby a risk of the operation is increased. Therefore, in the above embodiments, a width of each water injecting channel 11 is 2.5-4.2 mm preferably, and a height is 0.2-1 mm, the above width is a width of the effluent flow guiding component 9 extended along a circumferential direction of the outer wall of the tubular loop electrode 3, and the height is a height distance difference value between the inner wall of the effluent flow guiding component 9 and the outer wall of the tubular loop electrode 3.

Preferably, a front end part of the tubular loop electrode 3 is a curved structure, and an included angle α between a central axis of the front end part of the tubular loop electrode 3 and an axis of the water outlet holes 10 is 45-60 degrees, so the better view is acquired in the operation. Further preferably, the effluent flow guiding component 9 and the tubular loop electrode 3 are made of stainless steel with good electrical conductivity, not only the conductive reliability is guaranteed, but also rust is prevented, and it is beneficial to prolong service life and save the consumable cost, certainly, the effluent flow guiding component 9 and the tubular loop electrode 3 may also be manufactured by using an alloy with good electrical conductivity and anti-rust property or conductive metal coated with an anti-rust layer, for example an aluminum alloy. The effluent flow guiding component 9 is welded and fixed with the tubular loop electrode 3, and the connection is firm and reliable. In order to avoid the working electrode 2 from sticking to a human tissue in the operation process, the working electrode 2 is provided with an oleophobic layer.

In conclusion, the plasma operation electrode of the present invention has the good flow guiding effect to the normal saline, and is uniform and adequate in water supply, capable of effectively enhancing the electrical conductivity, effectively guaranteeing no current leakage in the position of contacting the tissue, high in reliability and safety, convenient to use, suitable for the resection operations of the tonsil and the adenoid, and strong in universality.

The above implementation modes are merely optimized implementation modes of the present invention, and not intend to limit a scope of protection of the present invention on this account, any non-substantial variations and substitutions made by those skilled in the art on the basis of the present invention fall within the scope of protection required by the present invention.

What is claimed is:

1. A plasma operation electrode for an otolaryngology department, comprising an insulating head, a working electrode, a tubular loop electrode, a water absorption tube, a handle, a water inlet hose, a water outlet hose and a lead; a reflowing hole is internally provided in the insulating head, one end of the insulating head is provided with the working electrode, and an other end of the insulating head is fixedly connected with the tubular loop electrode, and the tubular loop electrode is connected with an end part of the handle; the water absorption tube is sheathed in the tubular loop electrode, a water inlet channel is formed between the water absorption tube and the tubular loop electrode, and an end part of the water absorption tube is connected with the insulating head and communicated with the reflowing hole; the water inlet hose is installed in the handle and communicated with the tubular loop electrode, the water outlet hose is installed in the handle and communicated with the water absorption tube, and the lead passes through the handle and is connected with the tubular loop electrode, wherein the plasma operation electrode for the otolaryngology department further comprises an effluent flow guiding component; an end part, away from the handle, of the tubular loop electrode is provided with at least one water outlet hole; the effluent flow guiding component is correspondingly installed at the water outlet hole, and sealed and connected on an outer wall of the tubular loop electrode; a water injecting channel is formed between the effluent flow guiding component and the tubular loop electrode.

2. The plasma operation electrode for the otolaryngology department as claimed in claim 1, wherein one end of the effluent flow guiding component is connected to the outer wall of the tubular loop electrode, and the other end is extended to an end part, provided with the working electrode, of the insulating head.

3. The plasma operation electrode for the otolaryngology department as claimed in claim 2, wherein other parts, except a connecting part of two parties, on outer surfaces of the effluent flow guiding component and the tubular loop electrode are coated by an insulating layer, so that the tubular loop electrode is completely sealed.

4. The plasma operation electrode for the otolaryngology department as claimed in claim 1, wherein the effluent flow guiding component is an arc-shaped effluent flow guiding sheet; the water outlet hole is installed in a lower side of the tubular loop electrode, and the effluent flow guiding component is correspondingly sealed and installed at the lower side of the tubular loop electrode; and the water injecting channel is formed between the effluent flow guiding component and the tubular loop electrode.

5. The plasma operation electrode for the otolaryngology department as claimed in claim 1, wherein the effluent flow guiding component is the arc-shaped effluent flow guiding sheet; the end part, away from the handle, of the tubular loop electrode is provided with two water outlet holes, the water outlet holes are installed at an upper side and a lower side of the tubular loop electrode, the effluent flow guiding component is correspondingly sealed and installed at the upper side and the lower side of the tubular loop electrode, and corresponds to positions of the two water outlet holes; and the water injecting channel is respectively formed between the effluent flow guiding component and the upper side of the tubular loop electrode and between the effluent flow guiding component and the lower side of the tubular loop electrode.

6. The plasma operation electrode for the otolaryngology department as claimed in claim 1, wherein the end part, away from the handle, of the tubular loop electrode is symmetrically provided with at least two water outlet holes; the effluent flow guiding component is a tubular structure, the effluent flow guiding component is sealed and sheathed in a position, corresponding to the water outlet holes, of the tubular loop electrode, and a cross section of the water injecting channel which is formed between the effluent flow guiding component and the tubular loop electrode is annular.

7. The plasma operation electrode for the otolaryngology department as claimed in claim 1, wherein a width of the water injecting channel is 2.5-4.2 mm, and a height is 0.2-1 mm.

8. The plasma operation electrode for the otolaryngology department as claimed in claim 1, wherein a front end part, away from the handle, of the tubular loop electrode is a curved structure, and an included angle α between a central axis of the front end part of the tubular loop electrode and an axis of the water outlet hole is 45-60 degrees.

9. The plasma operation electrode for the otolaryngology department as claimed in claim 1, wherein the effluent flow guiding component and the tubular loop electrode are made of stainless steel, and the effluent flow guiding component is welded and fixed with the tubular loop electrode.

10. The plasma operation electrode for the otolaryngology department as claimed in claim 1, wherein the working electrode is provided with an oleophobic layer.

* * * * *